Jan. 7, 1958 F. MEILLAND Plant Pat. 1,673
ROSE PLANT
Filed April 29, 1957
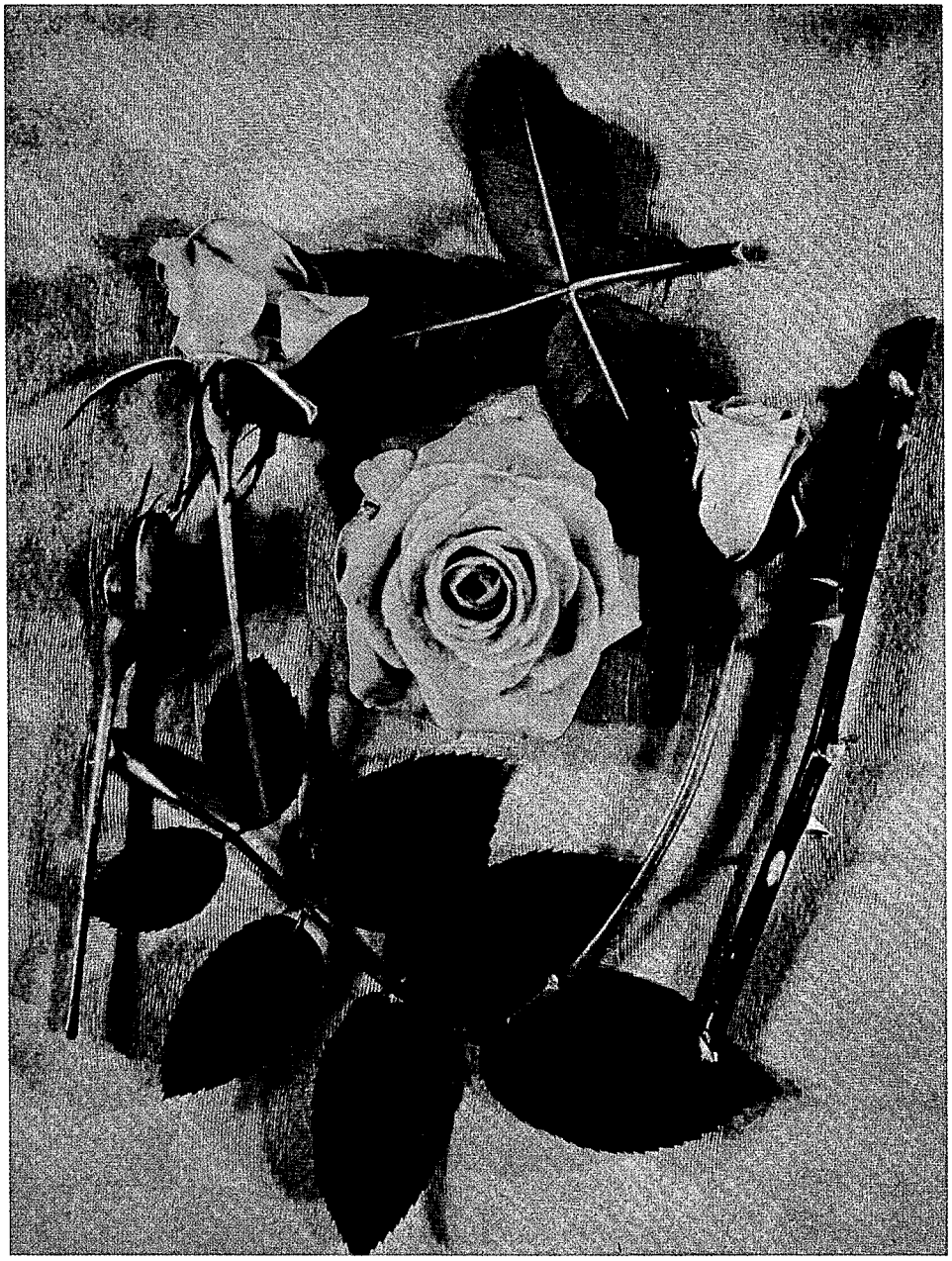
INVENTOR
Francis Meilland
BY Robb & Robb
ATTORNEYS United States Patent Office Plant Pat. 1,673
Patented Jan. 7, 1958

1,673

ROSE PLANT

Francis Meilland, Cap Azura, Cap d'Antibes, France, assignor to The Conard-Pyle Company, West Grove, Pa., a corporation of Pennsylvania Application April 29, 1957, Serial No. 655,931

1 Claim. (Cl. 47—61)

The present invention relates to a new and distinct variety of rose plant of the hybrid polyantha class, which was originated by me by crossing an unnamed and unpatented seedling of "Alain" (unpatented) × "Kordes Sondermeldung" (unpatented) with the variety "Moulin Rouge" (U. S. Plant Patent No. 1,298).

As the result of this breeding, I have produced a new rose variety which is particularly characterized as to novelty by the following features which are not present in combination in its parents or in any other variety of which I am aware:

(1) A strong and vigorous habit of growth, both in the garden and in the greenhouse, and the ability to make satisfactory growth in the greenhouse during the dark weather of winter seasons;

(2) The excellent foliage which shows better than average resistance to mildew and blackspot;

(3) The good form of the blooms which are more double than those of either parent;

(4) The intense Iridescent Scarlet general color tonality of the blooms which are brighter than those of either parent; and (5) The outstanding good keeping qualities of the flowers as greenhouse cut flowers.

Asexual reproduction of my new variety, as performed on my behalf by budding at West Grove, Pennsylvania, U. S. A., and by grafting at Richmond, Indiana, U. S. A., shows that the foregoing characteristics and distinctions come true to form and are established and transmitted through succeeding propagations.

The accompanying drawing shows typical specimens of the vegetative growth and the flowers of my new variety in different stages of development and as depicted in color as nearly true as it is reasonably possible to make the same in a color illustration of this character.

The following is a detailed description of the new variety, with color terminology in accordance with the Horticultural Colour Chart of the Royal Horticultural Society, except where general color terms of ordinary dictionary significance are obvious:

Type: Hardy; bush; outdoor; seedling; for cut flowers and for garden decoration.

Class: Hybrid polyantha.

Breeding: Seedling.

*Seed parent.*—An unnamed seedling of "Alain" × "Kordes Sondermeldung."

*Pollen parent.*—"Moulin Rouge."

Propagation: Holds its distinguishing characteristics through succeeding propagations by grafting and budding.

*Flower*

Locality where grown and observed: West Grove, Pennsylvania, U. S. A.

Flowers borne: Several to stem; in regular, flat clusters; on stems of medium length and normal strength.

Quantity of bloom: Free, both outdoors and in greenhouse.

Continuity: Continuous.

Fragrance: Slight.

Bud:

*Peduncle.*—Medium length; medium caliper; erect; rough; with medium number of brown hairs. Color — Scheele's Green, Plate 860/3, overlaid with Garnet Brown, Plate 00918/3 where exposed to sunlight.

*Before calyx breaks.*—Size—small. Form—medium length; pointed-ovoid; with a conspicuous neck; with foliaceous appendages on the surface of the bud; with slender, bristle-like foliaceous parts extending beyond the tip of the bud equal to ¼ or more of its length.

*As calyx breaks.*—Color—Scarlet, Plate 19, streaked with Currant Red, Plate 821, where first exposed to light.

*As first petal opens.*—Size—medium. Form—medium length; ovoid. Color: outside—Scarlet, Plate 19/1; inside—Vermilion, Plate 18, often streaked with Pod Green, Plate 061/2 at center of petal.

*Opening.*—Opens up well.

Bloom:

*Size (when fully open).*—From small to medium; from 1¾ to 2 inches.

*Petalage.*—Very double; from 65 to 75 petals; arranged regularly.

*Form.*—Full and high-centered at first, but becoming cupped to globular; petals being flat at first, but becoming loosely rolled outward later at maturity; in greenhouse, mature blooms often become globular.

Petals:

*Texture.*—Medium thickness.

*Appearance.*—Inside—velvety. Outside—satiny.

*Shape.*—Outer petals—broadly obovate; generally no notches. Intermediate petals—broadly obovate; generally no notches. Inner petals—usually undulate.

This description of a newly opened flower was made from a rose grown outdoors in the month of August, at West Grove, Pennsylvania, U. S. A.:

*Color.*—Outer petal: outside surface—Geranium Lake, Plate 20/1 at margin, shading to Carmine, Plate 21/1, and then to China Rose, Plate 024/2, with point of attachment Pod Green, Plate 061/2; inside surface—Iridescent Vermilion, Plate 18/1, shading to Rose Bengal, Plate 25/2 at base, with point of attachment Pod Green, Plate 061/2. Intermediate petal: outside surface—Geranium Lake, Plate 20/1, shading to China Rose, Plate 024/2, with point of attachment Pod Green, Plate 061/3; inside surface—Iridescent Scarlet, Plate 19, shading to Rose Bengal, Plate 25/2 at base, with point of attachment Chartreuse Green, Plate 663/3. Inner petal: outside surface—Geranium Lake, Plate 20/1, shading to Phlox Pink, Plate 625/1 at base; inside surface—Scarlet, Plate 19, with point of attachment Rose Pink, Plate 427/3, edged with Rose Bengal, Plate 25/2.

This description was made from a rose that was open for three days outdoors in the mouth of August, at West Grove, Pennsylvania, U. S. A.:

*Color.*—Outer petal: outside surface—broad margin of Scarlet, Plate 19/1, shading to Delft Rose, Plate 020/1, with point of attachment Pod Green, Plate 061/2; inside surface—Iridescent Vermilion, Plate 18, shading to China Rose, Plate 024/2 at base, with point of attachment Pod Green, Plate 061/1. Inner petal: outside surface—Geranium Lake, Plate 20/1, sometimes with streaks of Tyrian Rose, Plate 24/2, with point of attachment Pod Green, Plate 061/3; inside surface—Iridescent Scarlet, Plate 19, shading to China Rose, Plate 024/2, with point of attachment Pod Green, Plate 061/3.

*General color effect.*—Newly opened flower—Iridescent Scarlet, Plate 19. Three days open—Iridescent Scarlet, Plate 19.

*Behaviour.*—Drop off cleanly; grows and blooms well in greenhouse in winter.

*Flower longevity.*—On bush in garden—8 days in August. Cut roses grown outdoors and kept at living room temperatures—6 days in August. Cut roses grown in greenhouse and kept at living room temperatures—8 days in October.

*Reproductive organs*

Stamens: Medium number; arranged regularly about pistils.

Filaments: Many; most with anthers; medium length. Color—Barium Yellow, Plate 503/3.

Anthers: Open at various times; medium size; seldom an anther fused with a petaloid or a pistil. Color—Buttercup Yellow, Plate 5.

Pollen: Moderate quantity. Color—gold.

Pistils: Medium number.

Styles: Uneven; medium long; medium heavy; bunched.

Stigma: Color—white-yellow.

Ovaries: All enclosed in receptacle.

Hips: None.

Sepals: Permanent; moderately long; spear-shaped.

Seeds: None.

*Plant*

Foliage:

*Leaves.*—Compound of 5 or 7 leaflets; normal abundance; medium large; leathery.

*Leaflets.* — Shape — oval. Apex — acute. Base — acute. Margin—simply serrate.

*Color.*—Mature: upper surface—Spinach Green, Plate 0960; under surface—Grading from Sage Green, Plate 000861, to Sage Green, Plate 000861/1. Young: upper surface — Spinach Green, Plate 0960/2, heavily overlaid with Maroon, Plate 1030; under surface—Erythrite Red, Plate 0027, overlying Fern Green, Plate 0862.

*Rachis (the supporting stem of the compound leaf).*—Light. Upper side—grooved; hairy. Under side—moderately hairy.

*Stipules.*—Medium length; medium width; with points of medium length turning out at an angle of more than 90° generally; recurved towards the stem.

*Disease resistance.*—Better than average resistance to mildew and blackspot, as determined by comparison with other varieties grown under the same cultural conditions at West Grove, Pennsylvania, U. S. A.

Growth:

*Habit.*—Bushy; much-branched.

*Growth.*—Free.

*Canes.*—Medium caliper.

*Main stems.*—Color—between Spinach Green, Plate 0960, and Lettuce Green, Plate 861. Thorns—none botanically—see prickles. Prickles—several; color—Fern Green, Plate 0862/3. Hairs—none.

*Branches.*—Color—between Spinach Green, Plate 0960, and Lettuce Green, Plate 861. Thorns—none botanically—see prickles. Prickles—several; color—Fern Green, Plate 0862/3. Hairs—none.

*New shoots.*—Color—Lettuce Green, Plate 861/3, lightly overlaid with Oxblood Red, Plate 00823/3, where exposed to sun. Thorns—none botanically—see prickles. Prickles—several; color—Erythrite Red, Plate 0027. Hairs—none.

I claim:

A new and distinct variety of rose plant of the hybrid polyantha class, substantially as herein shown and described, characterized particularly as to novelty by its strong and vigorous habit of growth both outdoors and in the greenhouse, its ability to make satisfactory growth and bloom in the greenhouse during dark, winter weather, its excellent foliage and the better than average resistance thereof to mildew and blackspot, the good form of its blooms which are more double than those of either of its parents, the intense iridescent Scarlet general color tonality of its blooms and their greater brightness than those of either parent, and the outstandingly good keeping qualities of the blooms as greenhouse cut flowers.

No references cited.